United States Patent [19]

Weinstein

[11] Patent Number: 4,957,385
[45] Date of Patent: Sep. 18, 1990

[54] AMPULE SOLUTION DISPENSER APPLICATOR

[75] Inventor: Jack Weinstein, Manchester Township, Ocean County, N.J.

[73] Assignee: Primary Delivery Systems, Inc., Annandale, N.J.

[21] Appl. No.: 514,736

[22] Filed: Apr. 26, 1990

[51] Int. Cl.$^5$ .......................................... A61M 35/00
[52] U.S. Cl. ................................... 401/132; 401/134; 604/3; 206/530; 222/82
[58] Field of Search .................. 206/530, 532, 219; 215/226; 604/1, 2, 3; 222/82, 87, 89, 90, 187; 401/132, 133, 134, 135

[56] References Cited

U.S. PATENT DOCUMENTS

| | | | |
|---|---|---|---|
| 1,224,894 | 5/1917 | Berners | 401/132 |
| 2,642,065 | 6/1953 | Negri | 604/3 |
| 3,481,676 | 12/1969 | Schwartzman | 401/134 |
| 3,482,920 | 12/1969 | Schwartzman | 401/132 |
| 4,722,449 | 2/1988 | Dubach | 401/134 |
| 4,747,719 | 5/1988 | Parkin | 401/134 |
| 4,781,484 | 11/1988 | Goncalves | 401/132 |
| 4,784,506 | 11/1988 | Koreska | 401/134 |
| 4,929,109 | 5/1990 | Ikenaga | 401/133 |

FOREIGN PATENT DOCUMENTS

| | | | |
|---|---|---|---|
| 1059574 | 2/1967 | United Kingdom | 401/132 |

Primary Examiner—Richard J. Johnson
Attorney, Agent, or Firm—Kenneth P. Glynn

[57] ABSTRACT

The present invention is directed to an ampule solution dispenser applicator. It includes a container base, a plunger, an absorbent applicator and a cover. The container base has a collar or neck adapted to receive an ampule of a solution to be dispensed and the container is adapted to hold at least half of the ampule firmly. It also has an open area which would remain open surrounding an ampule upon insertion of an ampule into the container base and it has means for removably attaching a cover thereto. The plunger is adapted to be fitted over the collar of the base and adapted to have a first position resting on the collar and adapted to be forcibly permanently attached to the collar at a second position. The plunger includes means for holding an absorbent applicator such that a portion of the applicator is extending beyond the plunger and a portion of the applicator extends below the plunger into the container base. The plunger also has an extended wedge which is adapted to contact and break an ampule when the plunger is forced into its permanently attached second position on the collar of the base. When the cover is pushed onto the collar of the base, the plunger moves into the permanently attached second position and the wedge simultaneously breaks an ampule.

10 Claims, 2 Drawing Sheets

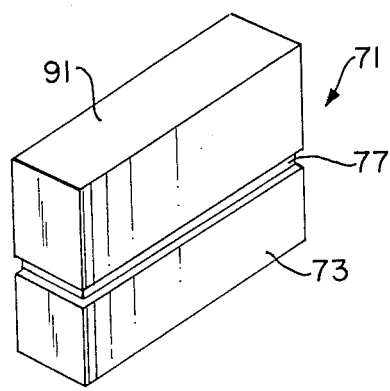
F I G. 4
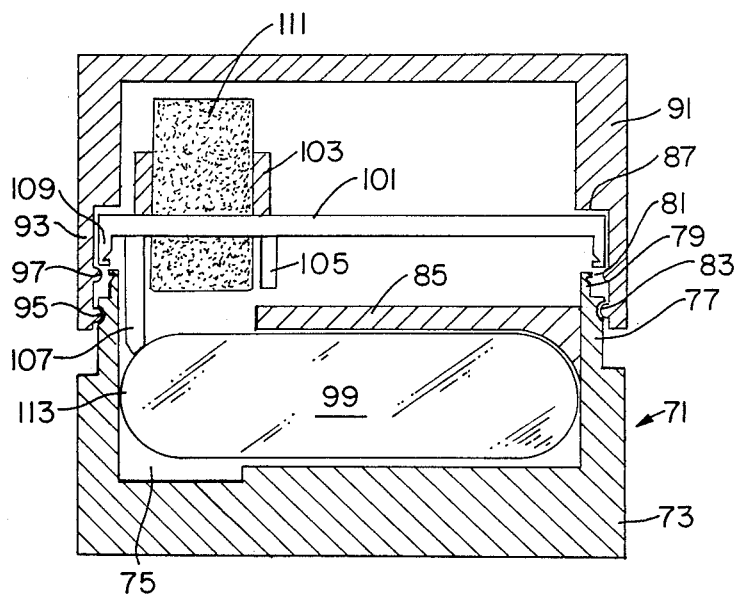
F I G. 5

AMPULE SOLUTION DISPENSER APPLICATOR

BACKGROUND OF THE INVENTION

1. Field of the Invention

The present invention is directed to an ampule solution dispenser applicator. More specifically, the present invention is directed to a dispenser applicator which constitutes a container for an ampule with a plunger top on the container for both breaking the ampule and bringing the applicator to the broken ampule for subsequent application. In general, the ampule solution dispenser applicator of the present invention may be used for any type of liquid applicator dispensing, such as nail polish, topical medication, surgical scrub, chemical testing, etc.

2. Prior Art Statement

The ability to pierce or break or otherwise enter into an ampule or container of solution at the time of its use enables a user to avoid evaporation, clogging and other problems which are inherent in prepunctured blotter or applicator type dispensers. Thus, numerous devices have been developed for puncturing a subcontainer or ampule with an applicator at the time of first use. For example, U.S. Pat. No. 3,481,676, issued to Schwartzman on Dec. 2, 1969 shows a system for piercing a subcontainer located within an applicator at the time of use by having an outer container with a series of bellows to enable the user to contract the container in such a way that a circular knife edge cuts into the inside container.

U.S. Pat. No. 4,747,719 to Parken describes a disposable topical application swab in which liquid which is initially stored within a tube or ampule is pierced with a lance which is connected to the inside of an outer tube. In this case, the cap of the outer tube holds the swab applicator and when the cap is removed, the punctured ampule and swab absorbent material is available for use. The cap in this prior art teaching has a first position and a second position, one for storing the innertube in an unpierced position and the second for storage and piercing.

U.S. Pat. No. 4,784,506 issued to Koreska et al on Nov. 15, 1988, describes a device for applying a predetermined quantity of liquid to a surface and involves the use of an applicator or swab as well as a breakable ampule. There are two flexible blades located along the sides so that the outer container may be squeezed so as to pierce the ampule and allow the liquid to then flow to the swab end of the device.

U.S. Pat. No. 3,482,920 to Schartzman issued on Dec. 9, 1969 shows a swab type or blotter type applicator container wherein a sealed container of liquid is pierced at the time of use by depressing a cap which contains a piercing element which passes through the resilient material and breaks the end of the previously sealed container. When the cap is removed the applicator has liquid flowing in a free flow fashion to the absorbent material.

U.S. Pat. No. 4,722,449 issued to Dubach on Feb. 2, 1988 describes a container with a flip cap which includes a strip section on the cap which is removed and then the cap is pushed down so as to cause an orifice in the cap to pierce an otherwise sealed container to free liquid. While this patent shows multiple positions for the cap, it does not involve the use of an ampule or a blotter material.

Notwithstanding the above cited prior art, the technology is lacking for a dispenser applicator which will simultaneously break the ampule and lock in the applicator while still providing for recapping or resealing capabilities. Thus, the prior art neither teaches nor renders obvious the ampule solution dispenser applicator of the present invention.

SUMMARY OF THE INVENTION

The present invention is directed to an ampule solution dispenser applicator. It includes a container base, a plunger, an absorbent applicator and a cover. The container base has a collar or neck adapted to receive an ampule of a solution to be dispensed and the container is adapted to hold at least half of the ampule firmly. It also has an open area which would remain open surrounding an ampule upon insertion of an ampule into the container base and it has means for removably attaching a covering thereto. The plunger is adapted to be fitted over the collar of the base and adapted to have a first position resting on the collar and adapted to be forcibly permanently attached to the collar at a second position. The plunger includes means for holding an absorbent applicator such that a portion of the applicator is extending beyond the plunger and a portion of the applicator extends below the plunger into the container base. The plunger also has an extended wedge which is adapted to contact and break an ampule when the plunger is forced into its permanently attached second position on the collar of the base. The absorbent applicator is, as indicated, located within the plunger so as to both extend into the container base and to extend outwardly beyond the plunger. The cover is adapted to a removably attached to the base and has side walls which include a ledge which is contactable with the top of the plunger such that when the cover is pushed onto the collar of the base, the plunger moves into the permanently attached second position and the wedge simultaneously breaks an ampule.

BRIEF DESCRIPTION OF THE DRAWINGS

The present invention as described herein will be more fully appreciated and understood when the specification is taken in conjunction with the appended drawings, wherein:

FIG. 4 shows an oblique frontal view of another embodiment of the present invention ampule solution dispenser applicator; and, FIG. 5 shows a side cut view of the ampule solution dispenser applicator shown in FIG. 4.

DETAILED DESCRIPTION OF THE INVENTION AND DRAWINGS

The present invention is directed to an ampule solution dispenser applicator. It is a dispenser in that it dispenses liquid or solution from an ampule and it is an applicator in that it provides for a resilient or absorbent material through which the liquid is applied. Thus, in a broad sense, the present invention may be used to apply any liquid desired by the applicator type method. This could involve writing implements, painting implements, make-up implements, implements for topical medicinal uses and any other purpose which the user may deem appropriate.

The ampule solution dispenser applicator of the present invention involves the ability of the user to simultaneously perform three functions.

Figure 1:
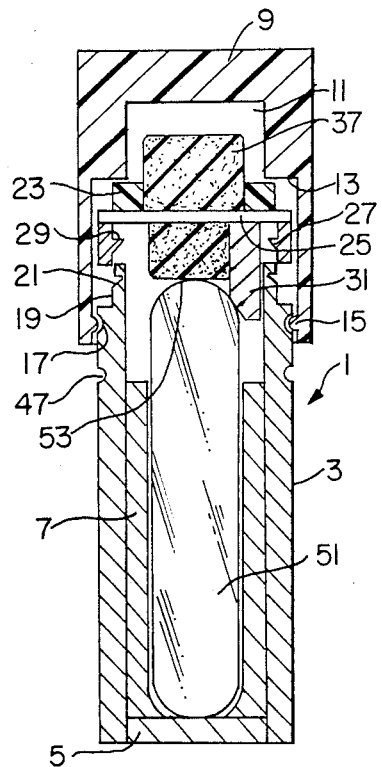
FIG. 1 shows a side cut view of one preferred embodiment of the ampule solution dispenser applicator of the present invention.

Referring now to FIG. 1, there is shown a present invention container applicator 1 which includes a container base 3 with a bottom 5. While these are shown as being made of two separate components, they could be of a single continuous molded product. Ampule support 7 is inserted therein permanently and may be glued or fused or nailed or otherwise held. Again, in the alternative, this could all be formed unistructurally. Cover 9 is shown which includes a cover clearance area 11 and has a cover wall ledge 13 and snap button 15 as shown. Snap button 15 is located in snap recess such as recess 17 located in base 3 as shown. Base collar 19 has a plunger lock recess such as recess 21. Plunger 23 includes an annular ring or flange 25 which holds absorbent applicator 37 such that part of 37 extends above plunger 23 and part of it extends below into base 3. Plunger wall 27 includes plunger lock 29, as shown. Plunger 23 also includes wedge 31 which has the geometry to fit against the top 53 of ampule 51 and, when the container applicator 1 is as shown in FIG. 1, plunger 23 is in a first position.

Figure 2:
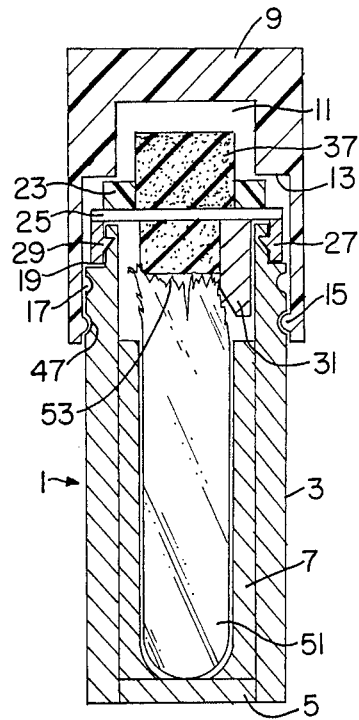
FIG. 2 shows a side cut view of the device shown in FIG. 1 but after the cover has been pushed down so as to cause the plunger to break the ampule.
Figure 3:
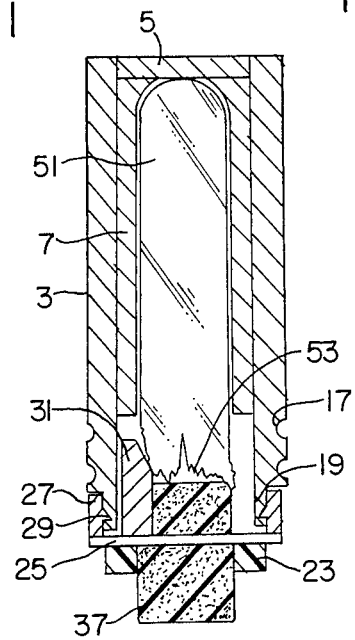
FIG. 3 shows a side cut view of the ampule solution dispenser applicator shown in FIGS. 1 and 2 but with the cover removed and ready for use.

The container applicator 1 shown in FIG. 1 is shown in FIG. 2 after force has been applied to cover 9 in a downward fashion. All like parts are like numbered and it should be noted that, in FIG. 2, plunger lock 29 is now locked into place as shown. Thus, three functions have been achieved simultaneously. Specifically, top 53 of ampule 51 has been broken by the pushing force of wedge 31. Second, the applicator 37 has been brought down into position next to the open ampule 51 to receive liquid as needed and, third, plunger 23 is now in its locked position. Cap 9 has been pressed down so that its snaps are now located in the lower snap recesses such as snap recess 47. However, cap 9 is easily removable and, although ledge 13 was utilized in pushing plunger 23 downward, there is no interlocking between plunger 23 and cap 9. Thus, when cap 9 is removed as shown in FIG. 3, the container applicator 1 may be inverted and is ready for application of the liquid by being dispensed from the ampule 51 to the absorbent applicator 37 for application thereof. As shown in FIG. 3 the inverted container applicator 1 has some of the parts numbered as in FIGS. 1 and 2.

Although the container applicator 1 of FIGS. 1 through 3 involve an ampule located in the vertical position, it should be noted that the ampule could be located in a different position such as at any angle between horizontal and vertical, or even in the horizontal position. This would simply depend upon the particular angle of the holder located within the base of the container itself. Thus, FIG. 4 shows a container applicator 71 which is rectangular in configuration and includes base 73 and cover 91. Base collar 77 is shown exposed in FIG. 4. FIG. 5 shows a side cut view of the container applicator 71 of FIG. 4. Herein, base 73 includes recess 75 along its collar 77 and collar extension 79 is adapted to lock plunger 101. Snaps 95 and 97 in cover 91 will fit into snap recesses such as snap recess 83 and plunger 101, with its plunger lock 109 will rest in a first position on base 73, as shown. Recess 75 is provided so that the end 113 of ampule 99 may subsequently be easily broken. Plunger 101 includes absorbent applicator holder annulus 103 which, as shown, holds absorbent applicator 111. Divider wall 105 is provided so that when plunger 101 is in its first position as shown, divider wall 105 is not in contact with base 73. However, when cover 91 is pushed downwardly, plunger lock 109 locks the plunger into place and divider wall 105 contacts ampule cover 85 directly to prevent liquid from inadvertently filling the void which would created to the right of divider wall 105. Further, plunger 101 also includes wedge 107 and when plunger 101 is forced into its second, permanently attached downward position, wedge 107 breaks end 113 of ampule 99. Further, applicator 111 comes into direct contact with broken ampule 99 and the liquid is absorbed up through the applicator and is available as needed. Although it is not drawn to scale, applicator 111 could have an extended portion or could be slanted so that its left side extends deep down into the area of where end 113 of ampule 99 is located.

It should be now seen that the exact shape of the container, its cross sectional configuration, the choice of materials of construction and its size are a matter of choice for the artisan. Also, while a single wedge is shown in the drawings, it may be beneficial to use a plurality of smaller wedges on one side of the ampule. Additionally, other changes may be made, such as the cap being a flip cap or a screw cap rather than a snap cap without exceeding the scope of the present invention.

What is claimed is:

1. An ampule solution dispenser applicator, which comprises:
   (a) a container base having a collar, and adapted to receive an ampule and adapted to hold at least half of said ampule firmly, and having an open area which would remain open surrounding an ampule upon insertion of an ampule, and further having means for removably attaching a cover thereto;
   (b) a plunger adapted to be fitted over the collar of said base and adapted to have a first portion resting on said collar and adapted to be forcibly permanently attached to said collar at a second position, said plunger including means for holding an absorbent applicator such that a portion of said applicator would extend beyond said plunger and a portion of said applicator would extend below said plunger into said base, said plunger further including an extended wedge adapted to contact and break an ampule upon said plunger being forced by pressure into its permanently attached said second position on the collar of said base;
   (c) an absorbent applicator located within said plunger and extending beyond said plunger and extending below said plunger into said base; and,
   (d) a cover adapted to be removably attached to said base, said cover having side walls and including a ledge located on said side walls which ledge is contactable with the top of said plunger such that when such cover is forcibly pushed onto the collar of said base, said plunger moves into the permanently attached second position on the collar of said base and said wedge of said plunger is movable therewith to break an ampule.

2. The ampule solution dispenser applicator of claim 1 wherein said means for removably attaching the cover to the base is one or more snap recesses located on one of the cover or base, and one or more corresponding snaps located on the other of said cover or base.

3. The ampule solution dispenser applicator of claim 1 which further comprises:
 (e) an ampule containing solution to be dispensed, said ampule being located within said container base.

4. The ampule solution dispenser applicator of claim 2 which further comprises:
 (e) an ampule containing solution to be dispensed, said ampule being located within said container base.

5. The ampule solution dispenser applicator of claim 1 wherein said container base is elongated and is adapted to receive an ampule in the vertical position.

6. The ampule solution dispenser applicator of claim 2 wherein said container base is elongated and is adapted to receive an ampule in the vertical position.

7. The ampule solution dispenser applicator of claim 1 wherein said container base is adapted to receive an ampule in the horizontal position.

8. The ampule dispenser applicator of claim 2 wherein said container base is adapted to receive an ampule in the horizontal position.

9. The ampule solution dispenser applicator of claim 1 wherein said cover is a snap cap having a first location corresponding to the first position of said plunger and a second location corresponding to the second position of said plunger.

10. The ampule solution dispenser applicator of claim 2 wherein said cover is a snap cap having a first location corresponding to the first position of said plunger and a second location corresponding to the second position of said plunger.

* * * * *